United States Patent [19]

Raghunathan

[11] Patent Number: 4,522,818

[45] Date of Patent: Jun. 11, 1985

[54] DIURETIC/ANTIHYPERTENSIVE COMPOSITIONS

[75] Inventor: Yegnaswami Raghunathan, Fairport, N.Y.

[73] Assignee: Pennwalt Corporation, Philadelphia, Pa.

[21] Appl. No.: 434,302

[22] Filed: Oct. 14, 1982

[51] Int. Cl.$^3$ ............................................ A61K 31/635
[52] U.S. Cl. ...................................... 514/155; 514/259
[58] Field of Search .................................. 424/229, 251

[56] References Cited

U.S. PATENT DOCUMENTS 3,081,230  3/1963  Weinstock et al. .................. 424/251
3,360,518  12/1967  Shetty .................................. 544/288

OTHER PUBLICATIONS

Matochik, T., Paper Submitted for Internship Research Credit at Pennwalt Corp.: *The In Vivo, In Vitro Analysis of a Fixed Combination Diuretic by Reversed Phase High Pressure Liquid Chromatography*, Sent to Rochester Institute of Technology 1979; on File in RIT Chemistry Library.

Di-Tab Bulletin, Stauffer Chemical Co., Aug. 1981.
Hohenegger, M. et al., *Int. J. Clin. Pharmacol.* 1976, 13(4), 298–303.
Onesti G., *Drug Therapy*, 66–78 (6/1975).
Zeller J., *Current Therapeutic Research*, 29(4), 45-1 to 45-8 (1981).
Hollifield J., et al., In *Systemic Effects of Antihypertensive Agents* (Sambhi M.–Editor), Symposia Specialists, 1976, pp. 131–155.
*Chemical Abstracts*, 85: 104041k (1976) [Hohenegger, M., et al., *Int. J. Clin. Pharmacol. Biopharm.* 1976, 13(4), 298–303].

Primary Examiner—Richard A. Schwartz

[57] ABSTRACT

A combination tablet containing metolazone and triamterene is useful in diuretic therapy and the treatment of hypertension. The composition is advantageous in the prevention of hypokalemia, a common side effect of diuretic therapy and possesses enhanced dissolution properties. Proper selection of the excipient formulation permits preparation of the tablets by direct compression.

7 Claims, 1 Drawing Figure

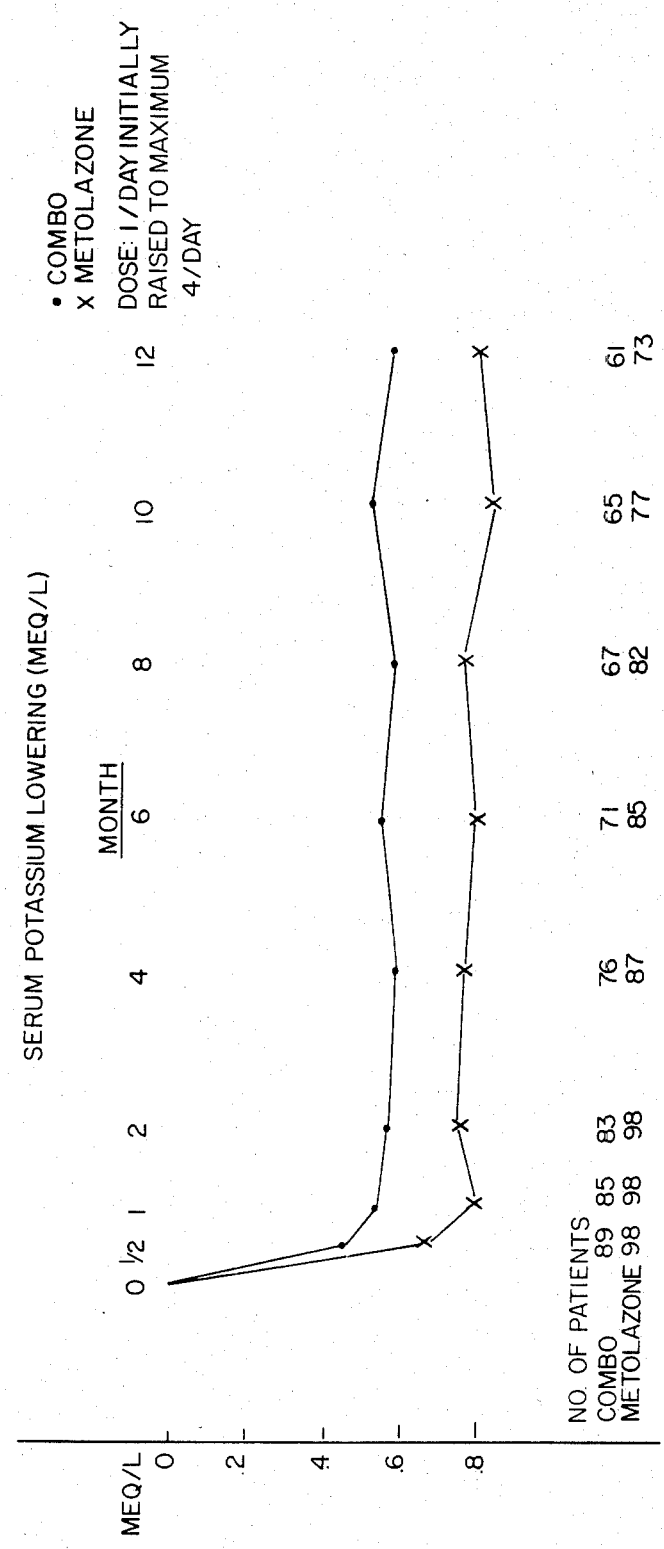

4,522,818

DIURETIC/ANTIHYPERTENSIVE COMPOSITIONS

BACKGROUND OF THE INVENTION

The diuretic, metolazone, is a sulfonamide derivative and chemically resembles the thiazide group of diuretics. Its chemical name is 2-methyl-3-o-tolyl-6-sulfamyl-7-chloro-1,2,3,4-tetrahydro-4-quinazolinone and it is described in U.S. Pat. No. 3,360,518 which is incorporated by reference. One side effect of metolazone is hypokalemia or abnormally low potassium levels in the blood. Triamterene, 2,4,7-triamino-6-phenylpteridine, is a pyrazine derivative which promotes the reabsorption of potassium while inhibiting sodium reabsorption in the distal tubule. Triamterene is described in U.S. Pat. No. 3,081,230 which is incorporated by reference. Triamterene also has a mild diuretic action of its own and when used with other common diuretics has been reported to have a synergistic effect in treating persons for hypertension. The concurrent administration of metolazone and triamterene to correct potassium losses resulting from the use of metolazone alone has been recommended in the literature, for example, Onesti "When Hypertension is Complicated", *Drug Therapy*, pp. 66–78 (1975). Zeller, "Efficacy of Metolazone in the Long-Term Treatment of Hypertensive Patients", *Current Therapeutic Research*, Vol. 29. No. 4 pp. 45-1 to 45-8 (1981), reported that triamterene had no significant effect on the reduction of potassium caused by metolazone use. However, Hollifield, "Some Biochemical Consequences of Diuretic Therapy of Low Renin Essential Hypertension", from "Systemic Effects of Antihypertensive Agents", M. P. Sambhi, Editor, *Symposia Specialists*, pp. 140 and 141 (1976) reports that triamterene administered along with metolazone blocked the kaliuresis induced by metolazone.

A common problem associated with solid dosage forms of metolazone and triamterene is their poor dissolution characteristics. I have found that a combination tablet containing a mixture of metolazone and triamterene is effective in the treatment of hypertension while reducing the hypokalemia which can result from the use of metolazone alone. The combination tablet unexpectedly possesses enhanced dissolution properties with respect to both metolazone and triamterene.

BRIEF SUMMARY OF THE INVENTION

In accordance with this invention there is provided a pharmaceutical preparation for the treatment of hypertension which comprises a mixture of metolazone, triamterene, and excipients.

Also provided is a method of treating hypertension comprising orally administering an effective dosage of a compressed combination tablet which includes a mixture of metolazone, triamterene and excipients.

The combination tablets can be prepared by a process of dry mixing, and direct compression where the excipients include at least about 2% by weight of the total weight of composition of a lubricant.

DESCRIPTION OF THE DRAWING

FIG. 1 is a graph illustrating the reduced serum potassium level lowering achieved by using the combination tablet of the invention compared with metolazone alone.

DETAILED DESCRIPTION

The composition of the drug mixture is chosen to provide tablets containing the diuretics metolazone and triamterene in weight ratios to provide the desired treatment of hypertension, while controlling the reduction of potassium due to metolazone, in a convenient dosage form. Each tablet is formulated to contain from about 0.025 to 2.5 percent by weight metolazone and from about 2.5 to 25 percent by weight of triamterene so that the ratio of metolazone to triamterene ranges from about 1:1 to 1:1000. An example of a suitable amount is about 2.5 mg of metolazone per 50 mg of triamterene in each tablet. The metolazone can range from about 0.1 to 10 mg per tablet and the triamterene from about 10 to 100 mg per tablet. The excipients include from about 72.5 to 97.0 percent by weight of the composition. The excipients conveniently range up to 89 mg for a 100 mg tablet and up to 778 mg for an 800 mg tablet. An example of a suitable amount of excipient, when using 50 mg of triamterene and 2.5 mg of metolazone per tablet, is about 348.5 mg.

The excipient system includes pharmacologically inert substances which provide properties necessary for the preparation of tablets such as compressibility, lubricity and flow of granules during compression to minimize sticking of the material to the tooling and die wall, and to provide a homogenous mixture of the active ingredients in the tablet. The excipients also should provide for the desired disintegration and dissolution characteristics of the tablet.

Suitable excipients include extenders such as dibasic calcium phosphate, sugars, and microcrystalline cellulose; disintegrants such as starch and microcrystalline cellulose; and lubricants such as talc, fatty acids, and salts of fatty acids. An example of suitable excipient mixtures include per tablet from about 0 to about 350 mg of unmilled dibasic calcium phosphate, from about 0 to 350 mg of microcrystalline cellulose, from about 0 to 150 mg of starch and from about 0 to 12 mg of calcium stearate.

Because of poor flow properties believed to be caused by the triamterene, a drug compaction method was developed in which the triamterene and part of the lubricant are pre-mixed and granulated in a compaction step before being added to the remainder of the batch. This provides a mixture having satisfactory flow properties to be fed to the tabletting machine without sticking. I have also found that by increasing the amount of lubricant to 2% by weight or more of the entire composition, the dry compaction step for triamterene can be eliminated while achieving excellent flow. Surprisingly, despite the presence of the increased amount of a hydrophobic lubricant material in this formulation, the enhanced solubility properties of the active ingredients are largely retained.

The invention is further illustrated by, but is not intended to be limited to, the following examples:

EXAMPLE 1

A pre-composition method to improve the flow of triamterene is illustrated. Total batch sizes to make 5,000 to 250,000 four hundred mg tablets have been used.

| Triamterene "Pre-Mix" | For 250,000 Tablets |
|---|---|
| Triamterene 50.0 mg/tablet | 12,500 g |

-continued

| Triamterene "Pre-Mix" | For 250,000 Tablets |
|---|---|
| Magnesium Stearate 2.0 mg/tablet | 500 g |

Procedure: The triamterene and magnesium stearate lubricant were mixed for 5 minutes in a blender and compressed using ½ inch flat faced beveled edge tooling. The resulting "slugs" were then passed through stainless steel screens fitted to an oscillator, first a #12 then a #60 screen (U.S. Standard Sieve Services). The triamterene granules were mixed with metolazone and the other excipients to make the combination tablet:

| Metolazone/Triamterene 2.5/50 Tablets | | For 250,000 Tablets |
|---|---|---|
| Metolazone Monocrystalline | 2.5 mg/tablet | 625 g |
| Triamterene "Pre-Mix" | 52.0 mg/tablet | 13,000 g |
| Unmilled Dibasic Calcium Phosphate | 144.5 mg/tablet | 36,125 g |
| Microcrystalline Cellulose (Avicel PH101) | 143.0 mg/tablet | 35,750 g |
| Sta-Rx 1500 starch U.S.P. | 40.0 mg/tablet | 10,000 g |
| Modified Starch (Explotab) | 16.0 mg/tablet | 4,000 g |
| Magnesium Stearate | 2.0 mg/tablet | 500 g |

Procedure: Mix the modified starch (Explotab) and the Sta-Rx 1500 starch for 10 minutes in a suitable size "double cone" blender. A geometric dilution of the metolazone (previously passed through a #3460 H.B. screen in a micro-pulverizer) was then made into this modified starch—Sta-Rx 1500 starch mix. The unmilled dibasic calcium phosphate and the microcrystalline celluloe (Avicel PH 101) were added to a Lodige mixer and mixed for 5 minutes without choppers. In the same Lodige mixer, the triamterene "pre-mix" was added and mixed 5 additional minutes, again without choppers. The starch-metolazone mix was then added to the Lodige and mixed for 15 minutes without choppers. Approximately 1 kg of this mix was pre-blended with the magnesium stearate, passed through a #30 mesh stainless steel screen and blended for 1½ minutes in the Lodige. The final granulation was then compressed using ⅜″ flat face beveled edge tooling. Initial physical parameters, assays and dissolutions on several lots are given in Table I.

EXAMPLE 2

This example illustrates a direct compression procedure for the formulation wherein the pre-compaction step for triamterene is eliminated.

| Metolazone/Triamterene 2.5/50 Tablets (direct compression formula) | | For 250,000 Tablets |
|---|---|---|
| Metolazone, Monocrystalline | 2.5 mg/tablet | 625 g |
| Triamterene | 50.0 mg/tablet | 12,500 g |
| Unmilled Dibasic Calcium Phosphate | 142.5 mg/tablet | 35,625 g |
| Microcrystalline Cellulose (Avicel Ph 101) | 141.0 mg/tablet | 35,250 g |
| Sta-Rx 1500 Starch U.S.P. | 40.0 mg/tablet | 10,000 g |
| Modified Starch (Explotab) | 16.0 mg/tablet | 4,000 g |
| Magnesium Stearate | 8.0 mg/tablet | 2,000 g |

Procedure: Mix the modified starch (Explotab) and the Sta-Rx 1500 starch for 10 minutes in a suitable size double cone blender. A geometric dilution of the metolazone (previously passed through a #3460 H.B. screen in a micro-pulverizer) was then made into this modified starch—Sta-Rx 1500 starch mix. The unmilled dibasic calcium phosphate and the microcrystalline cellulose were added to a Lodige mixer and mixed for 5 minutes without choppers. In the same Lodige mixer the triamterene was added and mixed for 5 additional minutes, again without choppers. The starch-metolazone mix was then added to the Lodige and mixed fifteen minutes without choppers. Approximately 1 kg of this mix was pre-blended with magnesium stearate, passed through a 30 mesh stainless steel screen, and blended for 3 minutes in the Lodige. The final granulation was then compressed using ⅜ inch flat face beveled edge tooling. Initial physical parameters, assays and dissolutions on several batches are given in Table II.

TABLE II

|  | 2A | 2B | 2C | 2D |
|---|---|---|---|---|
| Weight (mg) | 403 | 396 | 400 | 396 |
| Thickness (inches) | 0.169 | 0.165 | 0.165 | 0.167 |
| Hardness (kg) | 5.7 | 6.6 | 5.6 | 5.6 |
| Friability (%)* | 1.30 | 1.25 | 1.50 | 1.50 |
| Disintegration (sec.) USP Method | 66 | 50 | 54 | 45 |

TABLE I

|  | 1A | | 1B | | 1C | | 1D | | 1E | |
|---|---|---|---|---|---|---|---|---|---|---|
| Weight (mg) | 398 | | 400 | | 400 | | 400 | | 402 | |
| Thickness (inches) | 0.170 | | 0.171 | | 0.167 | | 0.167 | | 0.168 | |
| Hardness (kg) | 7.6 | | 6.0 | | 6.2 | | 4.9 | | 4.1 | |
| Friability (%)*** | 0.25 | | 0.10 | | 0.05 | | 1.0 | | 2.3 | |
| Disintegration (sec.) USP method | 25 | | 30 | | 54 | | 90 | | 117 | |
| Drug: | T* | M** | T | M | T | M | T | M | T | M |
| Assay (%): | 99.7 | 103.9 | 100.3 | 102.4 | 99.3 | 99.7 | 96.3 | 103.2 | 98.2 | 96.7 |
| Dissolution**** (% w/w) Time | | | | | | | | | | |
| 0.5 hr. | 64.6 | — | 52.9 | 17.3 | 44.9 | — | 44.7 | — | 32.2 | 20.6 |
| 1.0 hr. | 90.4 | 26.1 | 89.9 | 28.2 | 69.3 | 20.5 | 68.8 | 15.5 | 54.2 | 35.0 |
| 2.0 hr. | 98.8 | 36.4 | 97.7 | 39.7 | 85.2 | 31.0 | 88.6 | 26.8 | 74.5 | 52.5 |
| 3.0 hr. | 99.4 | 41.3 | — | 48.8 | 89.3 | 36.8 | 94.4 | 31.1 | 79.3 | 59.3 |
| 4.0 hr. | — | 44.4 | — | 52.6 | 91.2 | 39.9 | 96.1 | 33.6 | 79.4 | 63.5 |
| 6.0 hr. | — | 46.4 | — | 61.4 | — | — | — | 40.8 | 84.4 | 72.7 |

*Triamterence
**Metolazone
***Roche Friabilator 10 tablets, 10 minutes
****USP method, 900 ml, 0.1 N HCL, 50 rpm TABLE II-continued

| Drug | T+ | M++ | T | M | T | M | T | M |
|---|---|---|---|---|---|---|---|---|
| Assay (%) | 99.2 | 102.0 | 97.5 | 97.9 | 98.2 | 96.5 | 97.6 | 96.3 |
| Dissolution (% w/w)** Time | | | | | | | | |
| 0.5 hr. | 25.6 | 12.5 | 34.2 | 21.8 | 21.0 | 17.1 | 28.3 | 12.8 |
| 1.0 hr. | 35.8 | 20.8 | 41.2 | 30.6 | 33.7 | 28.7 | 38.4 | 27.9 |
| 2.0 hr. | 49.6 | 33.8 | 49.5 | 38.5 | 46.3 | 45.4 | 49.3 | 43.5 |
| 3.0 hr. | 57.3 | 43.8 | 53.9 | 45.2 | 51.6 | 52.8 | 54.0 | 51.8 |
| 4.0 hr. | 62.8 | 51.3 | 57.8 | 50.7 | 54.0 | 60.3 | 57.4 | 56.4 |
| 6.0 hr. | 67.7 | 61.9 | 63.6 | 59.3 | 60.6 | 70.0 | 65.1 | 64.5 |

*Roche Friabilator, 10 tablets, 10 minutes
**USP method, 900 ml, 0.1 N HCl, 50 rpm
+Triamterene
++Metolazone

EXAMPLE 3

Dissolution of Tablets

Both trimaterne and metolazone have limited solubility in aqueous solvents, and therefore currently available products containing these drugs individually exhibit slow dissolution. Surprisingly, however, the dissolutions of metolazone and triamterene from the formulation of the invention are much faster than the available products. This can be seen from the dissolution data in Table III.

TABLE III

| | Commercial Metolazone Tablets | Percent Dissolution* Metolazone Triamterene Tablets 2.5/50 mg Example 1C | | Commercial Triamterene Capsules |
|---|---|---|---|---|
| Time (hours) | 2.5 mg | Metolazone | Triamterene | |
| 0.25 | — | — | — | 0.751 |
| 0.50 | — | — | 44.9 | 3.15 |
| 1.00 | 2.81 | 20.5 | 69.3 | 7.53 |
| 2.00 | 4.56 | 31.0 | 85.2 | 21.0 |
| 3.00 | 5.94 | 36.8 | 89.3 | 34.4 |
| 4.0 | 7.23 | 39.9 | 91.2 | 45.4 |
| 6.0 | 8.74 | — | — | 61.1 |

*USP method, 900 ml, 0.1 N HCl, 50 rpm.

EXAMPLE 4

The clinical experience with the composition of this invention is illustrated.

FIG. 1 shows the mean serum potassium lowering values observed in patients maintained on either metolazone tablets (73–98 patients) or metolazone/triamterene 2.5/50 combination tablets (61–89 patients) for up to 12 months (one tablet initially raised to maximum 4 tablets daily). Patients on metolazone/triamterene tablets had less lowering of the serum potassium than patients on metolazone tablets. These differences were observed to be statistically significant.

EXAMPLE 5

The systolic and diastolic blood pressure changes in patients maintained on either metolazone/triamterene tablets (combo) or commercially available triamterene 50 mg/hydrochlorthiazide 25 mg capsules over 24 weeks of treatment were compared. Patients on metolazone/triamterene tablets showed significantly larger lowering of the systolic blood pressure values than patients on the capsules. The lowering of the diastolic blood pressure values in the patients on the two products were equivalent.

EXAMPLE 6

The fall in systolic and diastolic blood pressure values were compared in patients maintained for 8 weeks on:
(a) Metolazone/triamterene tablets (2.5/50 mg combo)
(b) Hydrochlorthiazide tablets
(c) Chlorthalidone tablets.

The lowering in systolic blood pressure values in patients on metolazone/triamterene tablets were more significant than in patients maintained on either hydrochlorthiazide or chlortholidone tablets.

The foregoing has described a novel pharmaceutical preparation which combines the active metolazone in the range of 0.1 to 10 mg per dose with the active triamterene in the range of 10 to 100 mg per dose to provide the desirable antihypertensive and diuretic properties without significant potassium imbalance and which provides a tablet with rapid disintegration and dissolution characteristics. By using an increased amount of lubricant in the excipient mixture a directly compressible composition is achieved in cases where triamterene of small particle size otherwise caused problems. While the description is directed to metolazone and triamterene, it should be understood that similar combinations of other closely related sulfonamide and pyrazine derivatives with antihypertensive activity which are described, for example, in U.S. Pat. Nos. 3,360,518 and 3,081,320 are considered to be within the scope of the invention.

What is claimed is:

1. A pharmaceutical preparation, useful in the treatment of hypertension, comprising a mixture of metolazone, triamterene and excipients, said mixture containing from about 0.025 to 2.5 percent by weight of metolazone, from about 2.5 to 25 percent by weight of triamterene, and from about 72.5 to 97.0 percent by weight of excipients consisting essentially of dibasic calcium phosphate, starch, microcrystalline cellulose and a lubricant.

2. The preparation of claim 1 wherein the weight ratio of metolazone to triamterene ranges from about 1:1 to 1:1000.

3. The preparation of claim 1 in the form of a compressed tablet wherein the mixture contains from about 0.1 to 10 mg of metolazone, from about 10 to about 100 mg of triamterene and from about 89 to 778 mg of excipients, wherein the excipients consist essentially of up to about 350 mg of dibasic calcium phosphate, up to about 350 mg of microcrystalline cellulose, up to about 150 mg of starch and up to 12 mg of lubricant.

4. The tablet of claim 3 wherein the lubricant is magnesium stearate.

5. The tablet of claim 4 containing about 2.5 mg of metolazone, about 50 mg of triamterene, and about 347.5 mg of excipients.

6. The preparation of claim 1 wherein the one hour dissolution of metolazone in aqueous 0.1N HCl is at least about 15 percent by weight and the one hour dissolution of triameterne in aqueous 0.1N HCl is at least about 30 percent by weight.

7. A method of treating hypertension, comprising orally administering to a person an effective dosage of a mixture of metolazone, triamterene and excipients, said mixture containing from about 0.025 to 2.5 percent by weight of metolazone, from about 2.5 to 25 percent by weight of triamterene, and from about 72.5 to 97.0 percent by weight of excipients consisting essentially of dibasic calcium phosphate, starch, microcrystalline cellulose and a lubricant.

* * * * *